(12) United States Patent
Hamaguchi et al.

(10) Patent No.: US 8,948,862 B2
(45) Date of Patent: Feb. 3, 2015

(54) STIMULATORY EFFECT ESTIMATION DEVICE, SLEEP DEPTH ESTIMATION DEVICE, STIMULATORY EFFECT ESTIMATION METHOD, AND VEHICLE CONTROL DEVICE

(75) Inventors: Takeshi Hamaguchi, Susono (JP); Kazuhide Shigeto, Susono (JP); Hisashi Iizuka, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 332 days.

(21) Appl. No.: 13/504,615

(22) PCT Filed: Mar. 11, 2010

(86) PCT No.: PCT/JP2010/054124
§ 371 (c)(1),
(2), (4) Date: Apr. 27, 2012

(87) PCT Pub. No.: WO2011/052245
PCT Pub. Date: May 5, 2011

(65) Prior Publication Data
US 2012/0253221 A1  Oct. 4, 2012

(30) Foreign Application Priority Data

Oct. 30, 2009  (JP) ................. 2009-250782

(51) Int. Cl.
*A61B 5/04* (2006.01)
*A61M 21/00* (2006.01)
(Continued)

(52) U.S. Cl.
CPC .................. *A61M 21/00* (2013.01); *A61B 5/00* (2013.01); *A61B 5/4812* (2013.01); *A61B 5/18* (2013.01);
(Continued)

(58) Field of Classification Search
CPC ............. A61B 5/0476; A61B 5/04012; A61B 5/0484; A61B 5/0482; A61B 5/4806; G08B 21/02; G08B 21/06; G08B 23/00
USPC ......... 600/544, 545; 340/573.1, 575
See application file for complete search history.

(56) References Cited

U.S. PATENT DOCUMENTS

2004/0193068 A1 * 9/2004 Burton et al. ............ 600/544
2005/0081847 A1 * 4/2005 Lee et al. ............. 128/200.24

FOREIGN PATENT DOCUMENTS

EP    1 859 736    11/2007
JP    6-190048    7/1994
(Continued)

OTHER PUBLICATIONS

Winter, Oscar et al. Auditory event-related potentials to deviant stimuli during drowsiness and stage 2 sleep. Electroencephalography and clinical Neurophysiology 96(1995) 398-412.*

(Continued)

*Primary Examiner* — Etsub Berhanu
(74) *Attorney, Agent, or Firm* — Finnegan, Henderson, Farabow, Garrett & Dunner, LLP

(57) ABSTRACT

A stimulatory effect estimation device includes a stimulus generator 3 which applies a stimulus to a back seat passenger, an electroencephalogram 2 which measures the brain waves of the back seat passenger, a memory 4, and an ECU 5 which specifies the brain wave indexes of stimulatory effects which surface in response to the stimuli both when the passenger is awake and when the passenger is asleep from the brain waves measured by the electroencephalogram 2 when a stimulus is applied from the stimulus generator 3 while the passenger is awake and the brain waves measured by the electroencephalogram 2 when a stimulus is applied from the stimulus generator 3 while the passenger is asleep. The ECU 5 estimates stimulatory effects when the passenger is asleep from stimulatory effects when the passenger is awake using a conversion model for converting the stimulatory effect when the passenger is awake and the stimulatory effects when the passenger is asleep on the basis of the brain wave indexes which surface when the same stimulus is applied when the passenger is awake and when the passenger is asleep, and selects a stimulus which is applied to the back seat passenger on the basis of the relationship between the stimulatory effects and the changes in sleep depth.

7 Claims, 20 Drawing Sheets

(51) Int. Cl.
  *A61B 5/00*   (2006.01)
  *A61B 5/18*   (2006.01)
  *A61B 5/0476* (2006.01)
  *A61B 5/0484* (2006.01)

(52) U.S. Cl.
  CPC ........... *A61B 5/0476* (2013.01); *A61B 5/04845* (2013.01); *A61B 5/4806* (2013.01); *A61B 5/6814* (2013.01); *A61B 5/4809* (2013.01); *A61M 2021/0027* (2013.01); *A61M 2021/0083* (2013.01); *A61M 2230/005* (2013.01); *A61M 2230/10* (2013.01); *Y02T 10/84* (2013.01)
  USPC .......................................... 600/545; 340/575

(56) References Cited

FOREIGN PATENT DOCUMENTS

| | | |
|---|---|---|
| JP | 7-108847 | 4/1995 |
| JP | 2002-28042 | 1/2002 |
| JP | 2002-28242 | 1/2002 |
| JP | 2006-297056 | 11/2006 |
| JP | 2007-117608 | 5/2007 |
| JP | 2008-49067 | 3/2008 |
| JP | 2008-194487 | 8/2008 |
| JP | 2009-213707 | 9/2009 |
| JP | 2009-213711 | 9/2009 |

OTHER PUBLICATIONS

Nordby, Helge et al. Event-related potentials (ERPs) to deviant auditory stimuli during sleep and waking. Neuroreport, Apr. 10, 1996;7(5):1082-1086.*
International Search Report in International Application No. PCT/JP2010/054124; Mailing Date: Apr. 6, 2010.
K. Campbell et al., "Event-related Potential Measures of the Disruptive Effects of Trains of Auditory Stimuli During Waking and Sleeping States," J. Sleep Res., vol. 14, pp. 347-357 (2005).
I. Okamoto et al., "Somatosensory ERP in Discrimination of Patterned Vibratory Stimuli in Persons with Visual Impairment" (2001).
M. Takahara et al., "Comparison of Event-related Potentials Between REM Sleep and the Sleep Onset Period" (2002).
I. Colrain et al., "The Use of Evoked Potentials in Sleep Research," Sleep Med Rev., vol. 11, No. 4, pp. 277-293 (Aug. 2007).
International Preliminary Report on Patentability for PCT/JP2010/054124 dated Jun. 21, 2012.
Bastuji, H. et al., "Evoked potentials as a tool for the investigation of human sleep," Sleep Medicine Reviews, vol. 3, No. 1, pp. 23-45, 1999.
Coenen, M. et al., "Auditory Evoked Potentials of Sleep-Wake States in Humans: A Qualitative psychophysiological Interpretation," Sleep-Wake Research in The Netherlands, Leiden University Press, Jan. 1, 2003, pp. 29-32.

* cited by examiner (a)

| N100 | DETERMINATION | PRESENT |
|------|---------------|---------|
| N350 | PRESENT | PRESENT |
| ABSENT | DEEP | LIGHT |

(a)

(b)

STIMULATORY EFFECT ESTIMATION DEVICE, SLEEP DEPTH ESTIMATION DEVICE, STIMULATORY EFFECT ESTIMATION METHOD, AND VEHICLE CONTROL DEVICE

CROSS-REFERENCE TO RELATED APPLICATIONS

This application is a national phase application of International Application No. PCT/JP2010/054124, filed Mar. 11, 2010, and claims the priority of Japanese Application No. 2009-250782, filed Oct. 30, 2009, the contents of both of which are incorporated herein by reference.

TECHNICAL FIELD

The present invention relates to a stimulatory effect estimation device, a stimulatory effect estimation method, and a vehicle control device which estimate the effects of a stimulus when a back seat passenger is asleep. The present invention also relates to a sleep depth estimation device which estimates a sleep depth.

BACKGROUND ART

A technique has hitherto been known in which, in order to wake a subject from a short sleep completely, a sleep rhythm is estimated from the amount of sweating of the subject, and after the subject has once reached a REM (Rapid Eye Movement) sleep, a stimulator is activated to wake the subject (for example, see Patent Literature 1).

CITATION LIST

Patent Literature

[Patent Literature 1] Japanese Unexamined Patent Application Publication No. 2002-028242

SUMMARY OF INVENTION

Technical Problem

On the other hand, when the subject is asleep, the content of ☐ waves in the brain waves is checked, thereby estimating the sleep depth of the subject. However, when the subject is asleep, it is difficult to evaluate stimulatory effects for stimuli of different types or intensities. For this reason, in the related art, in order to maintain the subject at a predetermined sleep depth, it may be impossible to determine the type and intensity of a stimulus to be applied. If the sleep depth is estimated on the basis of the content of δ waves, since the content of δ waves changes depending on the determination interval of the brain waves, there is a problem in that sufficient estimation precision may not be secured.

According to the technique described in Patent Literature 1, a stimulus is simply provided after the subject is asleep, and there is no description of a method of setting or controlling a stimulus. There is no consideration of the effects for the type or intensity of a stimulus when the subject is asleep.

Accordingly, an object of the invention is to provide a stimulatory effect estimation device, a stimulatory effect estimation method, and a vehicle control device capable of predicting stimulatory effects when a subject is asleep, and to provide a sleep depth estimation device capable of estimating a sleep depth with high precision without being affected by the estimation timing of the sleep depth.

Solution to Problem

The inventors have carefully studied and have found that, since the access route of neural pulses from the brain by a stimulatory response is the same between when the subject is awake and when the subject is asleep, the brain wave indexes which surface both when the subject is awake and when the subject is asleep while a stimulus is applied are used to predict stimulatory effects when the subject is awake from stimulatory effect when the subject is asleep.

Accordingly, a stimulatory effect estimation device according to the invention includes a stimulus generation unit which applies a stimulus to a subject, a brain wave measurement unit which measures the brain waves of the subject, and a stimulatory effect estimation unit which specifies the brain wave indexes of stimulatory effects which surface in response to the stimuli both when the subject is awake and when the subject is asleep from the brain waves measured by the brain wave measurement unit when a stimulus is applied from the stimulus generation unit while the subject is awake and the brain waves measured by the brain wave measurement unit when a stimulus is applied from the stimulus generation unit while the subject is asleep.

With the stimulatory effect estimation device according to the invention, the brain wave indexes of the stimulatory effects which surface in response to the stimuli both when the subject is awake and when the subject is asleep, thereby associating the stimulatory effects when the subject is awake with the stimulatory effects when the subject is asleep. Therefore, since the stimulatory effects can be converted between when the subject is awake and when the subject is asleep, it is possible to convert the stimulatory effects when the subject is asleep from the stimulatory effects when the subject is awake.

The stimulatory effect estimation unit may estimate stimulatory effects when the subject is asleep from stimulatory effects when the subject is awake using a conversion model for converting the stimulatory effect when the subject is awake and the stimulatory effects when the subject is asleep on the basis of the brain wave indexes which surface when the same stimulus is applied when the subject is awake and when the subject is asleep, and may select a stimulus which is applied to the subject on the basis of the relationship between the stimulatory effects and the changes in sleep depth. With this configuration, the brain wave indexes which surface both when the subject is awake and when the subject is asleep while the same stimulus is applied, thereby creating the conversion model for converting the stimulatory effects when the subject is awake and the stimulatory effects when the subject is asleep. With the use of the created conversion model, it is possible to estimate the stimulatory effects when the subject is asleep from the stimulatory effects when the subject awake. Accordingly, a stimulus which is applied to the subject is obtained on the basis of the relationship between the stimulatory effects and the changes in sleep depth, thereby controlling the sleep depth of the subject. Therefore, for example, it is possible to maintain the sleep state of the subject in a light sleep state.

The stimulatory effect estimation unit may correct the stimulatory effects on the basis of the amplitude of a specific brain wave. Usually, a specific brain wave, such as α wave generated in an eye closure state or the like when the subject is awake, does not significantly change in amplitude. Accordingly, for example, the stimulatory effects are corrected on the basis of the amount of relative change in the amplitude of the brain wave index with respect to the amplitude of the specific brain wave, thereby excluding the influence of a measurement error of the brain wave measurement unit, the physical shape of the subject, or the like and appropriately estimating the stimulatory effects when the subject is asleep.

The stimulatory effect estimation unit may select the parameters of a stimulus which is applied when the subject is asleep on the basis of the stimulatory effects when the subject is awake. When the subject is asleep, since the state of the subject, such as the sleep depth, frequently changes due to a stimulus, a time elapse, or the like, it becomes difficult to evaluate stimulatory effects for a stimulus when the subject is asleep. Accordingly, the stimulatory effect when the subject is asleep can be estimated from the stimulatory effects when the subject is awake. Therefore, the parameters of a stimulus which is applied when the subject is asleep are selected on the basis of the stimulatory effects when the subject is awake, thereby excluding the influence of a change in the sleep state of the subject when selecting a stimulus which is applied to the subject.

It is preferable that the stimulatory effect estimation unit selects the parameters of a stimulus which is applied when the subject is asleep on the basis of stimulatory effects for a stimulus of different parameters. In this way, the parameters of a stimulus to be applied are selected on the basis of stimulatory effects for a stimulus of different parameters. For this reason, for example, when there are a plurality of stimuli of the same stimulus intensity, the parameters of a stimulus for which the highest stimulatory effects surface from among the stimuli are utilized, thereby efficiently generating a stimulus. When there are a plurality of stimuli for which the same stimulatory effects surface, a stimulus with the lowest stimulus intensity from among the stimuli is selected, thereby selecting a stimulus with a little sense of discomfort without degrading the stimulatory effects.

It is preferable that the stimulatory effect estimation unit changes the parameters of a stimulus which is applied when the subject is asleep on the basis of stimulatory effects when a stimulus of a specific parameter continues to be applied. Although if the same stimulus continues to be applied, the stimulatory effects are degraded habitually, the parameters of a stimulus to be applied changes on the basis of the stimulatory effects when a stimulus of a specific parameter continues to be applied, thereby preventing the stimulatory effects from being degraded habitually.

It is preferable that the stimulatory effect estimation unit estimates the sleep depth of the subject on the basis of the measurement result of brain waves for a stimulus applied to the subject. In this way, the sleep depth is estimated on the basis of the response of the brain waves for a stimulus applied to the subject, thereby estimating the sleep depth with high precision without being affected by the estimation timing of the sleep depth.

A sleep depth estimation device according to the invention includes a stimulus generation unit which applies a stimulus to a subject, a brain wave measurement unit which measures the brain waves of the subject, and a sleep depth estimation unit which estimates the sleep depth of the subject on the basis of the response of brain waves for a stimulus applied to the subject.

In the related art, the sleep depth is estimated from the content of δ waves which surface during a predetermined period. With regard to the estimation in the related art, since the content of δ waves changes depending on the setting of the determination interval, accurate estimation may not be performed. Accordingly, the inventors have carefully studied on the improvement in the estimation precision of the sleep depth and have found that, if a stimulus is applied when the subject is asleep, the stimulatory effects differ depending on the sleep depth. That is, it has been found that, if a stimulus is applied when the subject is asleep, there are brain wave indexes which surface both when the subject takes a light sleep and when the subject takes a deep sleep, while there are brain wave indexes which do not surface when the subject takes a light sleep but surface when the subject takes a deep sleep. Accordingly, with the sleep depth estimation device according to the invention, the sleep depth is estimated on the basis of the response of the brain waves for a subject applied to the subject, thereby estimating the sleep depth with high precision without being affected by the estimation timing of the sleep depth.

A stimulatory effect estimation method according to the invention includes the steps of generating a stimulus when a subject is awake to acquire the brain waves of the subject, generating a stimulus when the subject is asleep to acquire the brain waves of the subject, and specifying the brain wave indexes of stimulatory effects which surface in response to the stimuli both when the subject is awake and when the subject is asleep.

With the stimulatory effect estimation method according to the invention, the brain wave indexes of the stimulatory effects which surface in response to the stimuli both when the subject is awake and when the subject is asleep are specified, thereby associating the stimulatory effects when the subject is awake with the stimulatory effects when the subject is asleep. Therefore, it possible to convert the stimulatory effects between when the subject is awake and when the subject is asleep, thereby converting the stimulatory effect when the subject is asleep from the stimulatory effects when the subject is awake.

It is preferable that stimulatory effects when the subject is asleep are estimated from stimulatory effects when the subject is awake using a conversion model for converting the stimulatory effect when the subject is awake and the stimulatory effects when the subject is asleep on the basis of the brain wave indexes which surface when the same stimulus is applied when the subject is awake and when the subject is asleep, and a stimulus which is applied to the subject is selected on the basis of the relationship between the stimulatory effects and the changes in sleep depth. With this configuration, the brain wave indexes which surface both when the subject is awake and when the subject is asleep while the same stimulus is applied are specified, thereby creating the conversion model for converting the stimulatory effects when the subject is awake and the stimulatory effects when the subject is asleep. With the use of the created conversion model, it is possible to estimate the stimulatory effects when the subject is asleep from the stimulatory effects when the subject is awake. Accordingly, a stimulus which is applied to the subject is obtained on the basis of the relationship between the stimulatory effects and the changes in sleep depth, thereby controlling the sleep depth of the subject. Therefore, for example, it is possible to maintain the sleep state of the subject in a light sleep state.

A vehicle control device according to the invention includes a stimulus generation unit which applies a stimulus to a passenger, a brain wave measurement unit which measures the brain waves of the passenger, and a stimulatory effect estimation unit which specifies the brain wave indexes of stimulatory effects which surface in response to the stimuli both when the passenger is awake and when the passenger is asleep from the brain waves measured by the brain wave measurement unit when a stimulus is applied from the stimulus generation unit while the passenger is awake and the brain waves measured by the brain wave measurement unit when a stimulus is applied from the stimulus generation unit while the passenger is asleep, estimates stimulatory effects when the passenger is asleep from stimulatory effects when the passenger is awake using a conversion model for converting the stimulatory effect when the passenger is awake and the stimulatory effects when the passenger is asleep on the basis of the brain wave indexes which surface when the same stimulus is applied when the passenger is awake and when the passenger is asleep, and selects a stimulus which is applied to the passenger on the basis of the relationship between the stimulatory effects and the changes in sleep depth.

With the vehicle control device according to the invention, the brain wave indexes of the stimulatory effects which surface in response to the stimuli both when the passenger is awake and when the passenger is asleep are specified, thereby associating the stimulatory effects when the passenger is awake with the stimulatory effects when the passenger is asleep. Thus, it is possible to convert the stimulatory effects between when the passenger is awake and when the passenger is asleep, thereby converting the stimulatory effects when the passenger is asleep from the stimulatory effects from when the passenger is awake. The brain wave indexes which surface both when the passenger is awake and when the passenger is asleep while the same stimulus is applied are specified, thereby creating the conversion model for converting the stimulatory effects when the passenger is awake and the stimulatory effects when the passenger is asleep. With the use of the created conversion model, it is possible to estimate the stimulatory effects when the passenger is asleep from the stimulatory effects when the passenger is awake. Accordingly, a stimulus which is applied to a passenger is obtained on the basis of the relationship between the stimulatory effects and the changes in sleep depth, thereby controlling the sleep depth of the passenger. Therefore, for example, it is possible to maintain the sleep state of the passenger in a light sleep state, thereby allowing an efficient short sleep in a short period and suppressing response reduction after the passenger is awake.

Advantageous Effects of Invention

According to the invention, it is possible to estimate the stimulatory effects when the subject is asleep. According to the invention, it is possible to estimate the sleep depth with high precision without being affected by the estimation timing of the sleep depth.

BRIEF DESCRIPTION OF DRAWINGS

FIG. 16 is a diagram showing the relationship between the presence/absence of appearance of a brain wave index and sleep depth.

DESCRIPTION OF EMBODIMENTS

Figure 1:
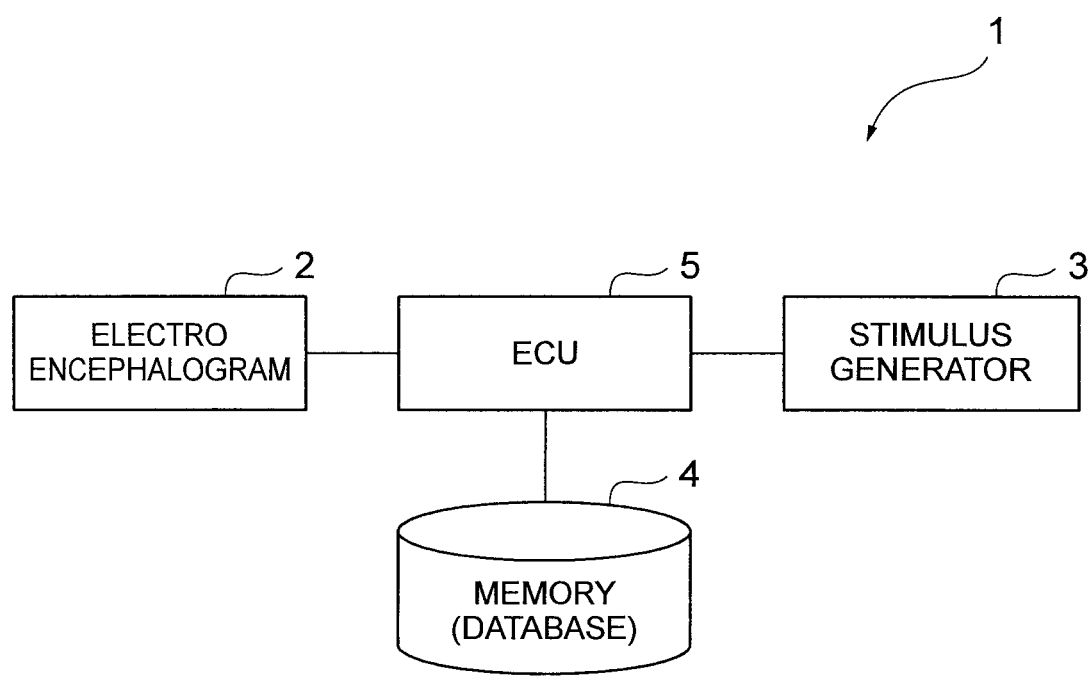
FIG. 1 is a diagram showing the schematic configuration of a vehicle control device according to this embodiment.

Hereinafter, a preferred embodiment of a stimulatory effect estimation device, a stimulatory effect estimation method, and a vehicle control device according to the invention will be described in detail with reference to the drawings. This embodiment is a technique for controlling a sleep depth during a non-REM sleep, and a stimulatory effect estimation device, a sleep depth estimation device, a stimulatory effect estimation method, and a vehicle control device according to the invention are applied to a vehicle control device which maintains the sleep depth of a back seat passenger who takes a short sleep in a light sleep state (sleep depth I and II) during the non-REM sleep. In the drawings, the same or equivalent parts are represented by the same reference numerals.

[First Embodiment]

FIG. 1 is a diagram showing the schematic configuration of a vehicle control device of this embodiment. As shown in FIG. 1, a vehicle control device 1 of this embodiment includes an electroencephalogram 2, a stimulus generator 3, a memory 4, and an ECU 5.

The electroencephalogram 2 is a device which measures a slight potential difference (about several 10 µV) which is generated in the head region of a back seat passenger to measure the brain waves of the back seat passenger. If the brain waves are measured, the electroencephalogram 2 transmits the brain waves to the ECU 5.

The stimulus generator 3 is a device which generates a stimulus under the control of the ECU 5. Although in this embodiment, a case where the stimulus generator 3 generates an acoustic stimulus will be described, any stimulus, such as current, wind, smell, or light, may be generated insofar as a stimulus can be applied to the back seat passenger.

The memory 4 is a storage device which accumulates various kinds of information, and stores a conversion model described below, a database, or the like on the basis of an instruction of the ECU 5.

The ECU 5 is electrically connected to the electroencephalogram 2, the stimulus generator 3, and the memory 4. The ECU 5 causes the stimulus generator 3 to generate a stimulus, acquire the brain waves of the back seat passenger measured by the electroencephalogram 2 to select the parameters of a stimulus, estimates stimulatory effects when the back seat passenger is asleep, and maintains the sleep depth of the back seat passenger who takes a short sleep in a light sleep state.

Figure 2:
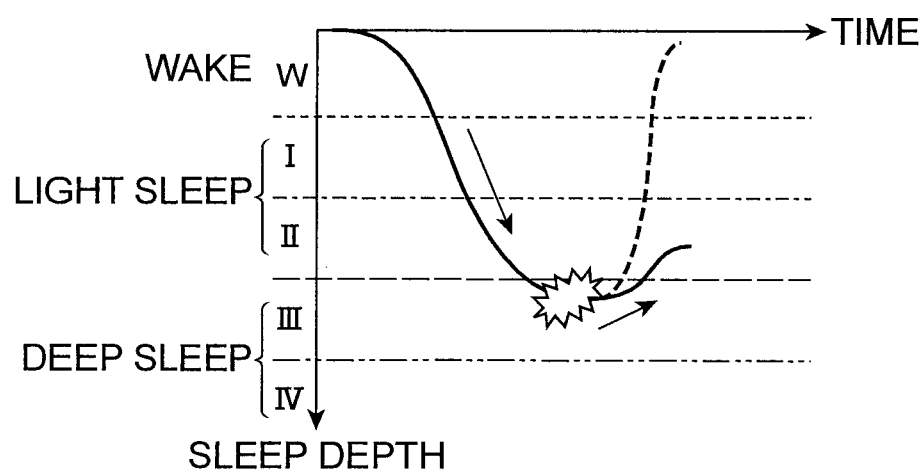
FIG. 2 is a diagram showing the relationship between a sleep depth and a change in a sleep state.

FIG. 2 is a diagram showing the relationship between sleep depth and a change in a sleep state. In FIG. 2, W, I, II, III, and IV represent sleep depth based on the international standard. The sleep depth W represents a wake state (awake), the sleep depth I and II represent a light sleep, and the sleep depth III and IV represent a deep sleep. As shown in FIG. 2, if the back seat passenger gets to sleep, the sleep depth (sleep state) changes inconstantly. At this time, in the case of a sleep in a short time, such as a short sleep, if the passenger falls into a deep sleep, it may be impossible to wake the passenger from the deep sleep completely. Accordingly, if the sleep state of the back seat passenger who takes a short sleep reaches a deep sleep, the ECU 5 causes the stimulus generator 3 to generate a stimulus, such that the back seat passenger does not fall into a deep sleep.

Figure 3:
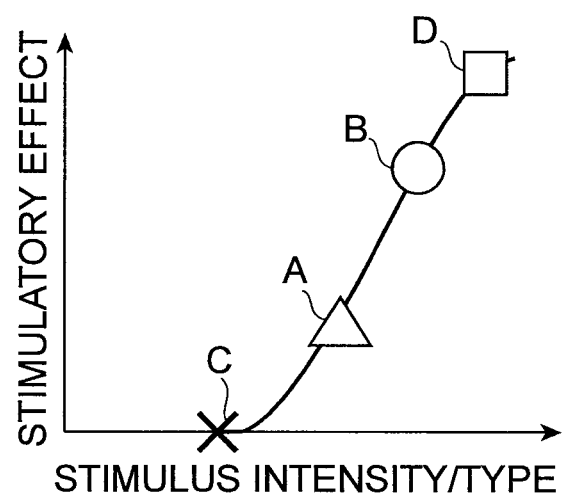
FIG. 3 is a diagram showing the relationship between the type/intensity of a stimulus and stimulatory effects when a back seat passenger is awake.
Figure 4:
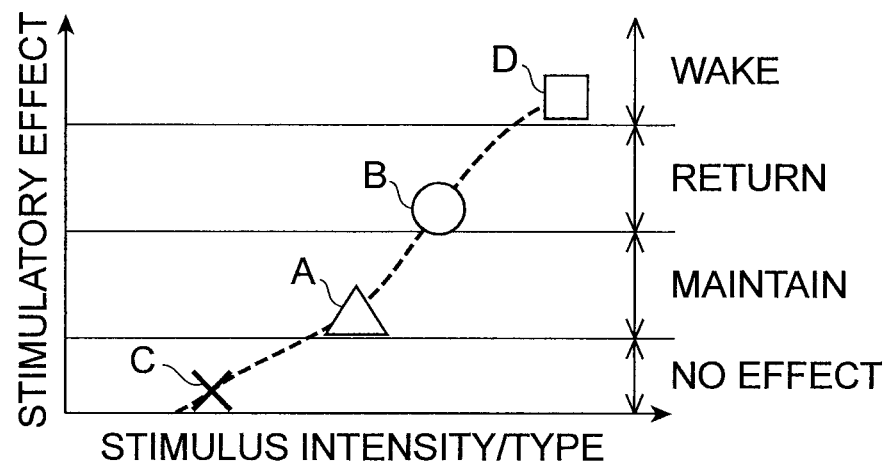
FIG. 4 is a diagram showing the relationship between the type/intensity of a stimulus and stimulatory effect when a back seat passenger is asleep.

FIG. 3 is a diagram showing the relationship between the type/intensity of a stimulus and stimulatory effect when a back seat passenger is awake. FIG. 4 is a diagram showing the relationship between the type/intensity of a stimulus and stimulatory effects when a back seat passenger is asleep. In FIGS. 3 and 4, A, B, C, and D represent stimuli of different types or intensities. As shown in FIGS. 3 and 4, stimulatory effects change depending on the type of a stimulus or the intensity of a stimulus, and when the back seat passenger is asleep, the sleep state changes depending on the type of a stimulus or the intensity of a stimulus.

As shown in FIG. 2, if a stimulus is applied when the sleep depth reaches III, the sleep depth returns to II or the passenger is awake depending on the type or intensity of the stimulus. For this reason, in order to maintain the sleep state in a light sleep state, it is necessary to estimate stimulatory effects when the back seat passenger is asleep based on the type or intensity of the stimulus, and there is demand for estimating stimulatory effects when the back seat passenger is asleep from the stimulatory effects when the back seat passenger is awake.

Accordingly, the ECU 5 specifies the brain wave indexes of stimulatory effects which surface in the brain waves both when the back seat passenger is awake and when the back seat passenger is asleep while the same stimulus is applied, and creates a conversion model for converting the stimulatory effects when the back seat passenger is awake and the stimulatory effects when the back seat passenger is asleep on the basis of the specified brain wave indexes.

Here, the creation of the conversion model will be described in detail.

Figure 5:
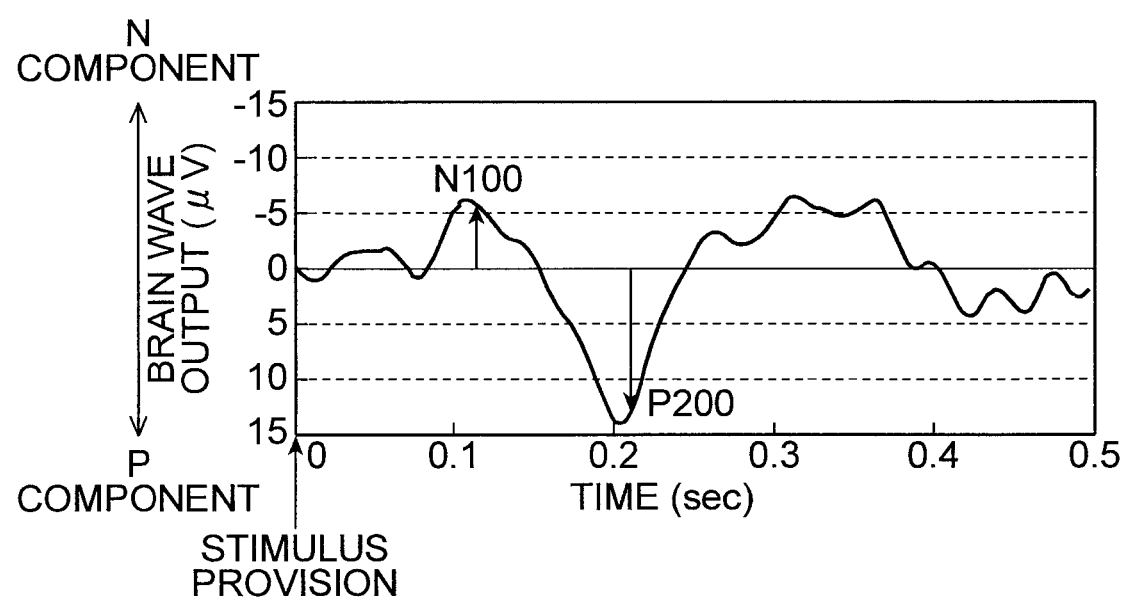
FIG. 5 is a diagram showing brain waves until a predetermined time elapses after a stimulus is applied.

First, stimulatory effects which surface in the brain waves will be described with reference to FIG. 5. FIG. 5 is a diagram showing brain waves until a predetermined time elapses after a stimulus is applied. In FIG. 5, the horizontal axis represents time (sec) after a stimulus is generated (provided), and the vertical axis represents the output of brain waves (μV) measured by the electroencephalogram 2. The time after a stimulus is generated on the horizontal axis is usually called latent time. As shown in FIG. 5, with regard to the brain waves, a slight potential difference which is generated in the head region of a person is measured by the electroencephalogram 2. The brain waves include brain waves which are generated spontaneously and brain waves which are induced by a stimulus. The latter brain waves which are induced by a stimulus become brain wave indexes representing stimulatory effects. For this reason, the latent time or amplitude of the brain wave indexes is measured, thereby evaluating stimulatory effects.

The brain wave indexes are expressed by a combination of the polarity of the peak (apex) and the latent time until a peak appears after a stimulus is applied. For example, N100 represents the brain wave indexes in a negative direction which are observed around the latent time of 100 msec, and P200 represents the brain wave indexes in a positive direction which are observed around the latent time of 200 msec. When the brain waves are expressed by a graph, in general, the negative direction is upward, and the positive direction is downward. It is thought that a P component represents determination for a stimulus, and an N component represents a simple response for a stimulus.

Figure 6:
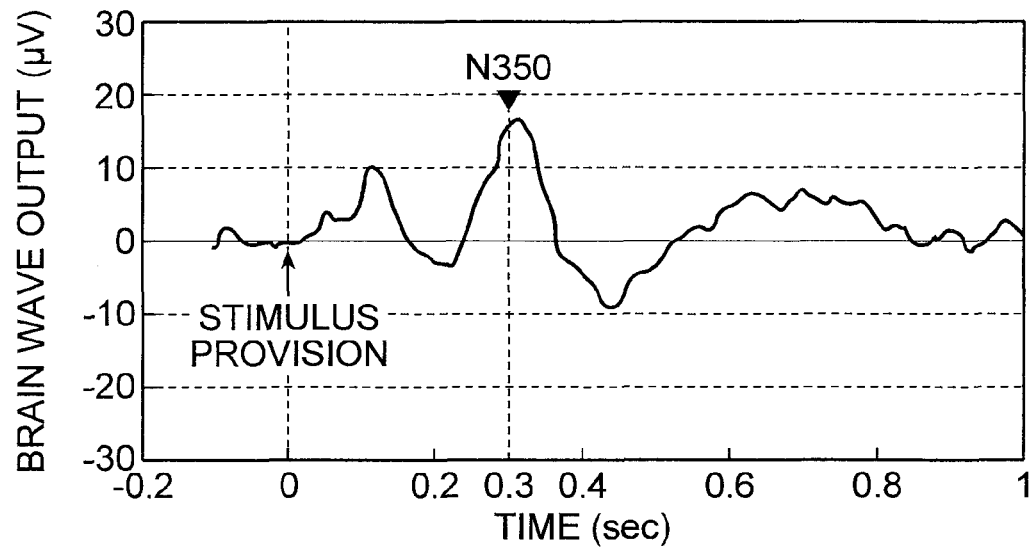
FIG. 6 is a diagram showing brain wave indexes for an acoustic stimulus, specifically, FIG. 6(*a*) shows brain waves measured when a back seat passenger is awake, and FIG. 6(*b*) shows brain waves measured when a back seat passenger is asleep.
Figure 6:
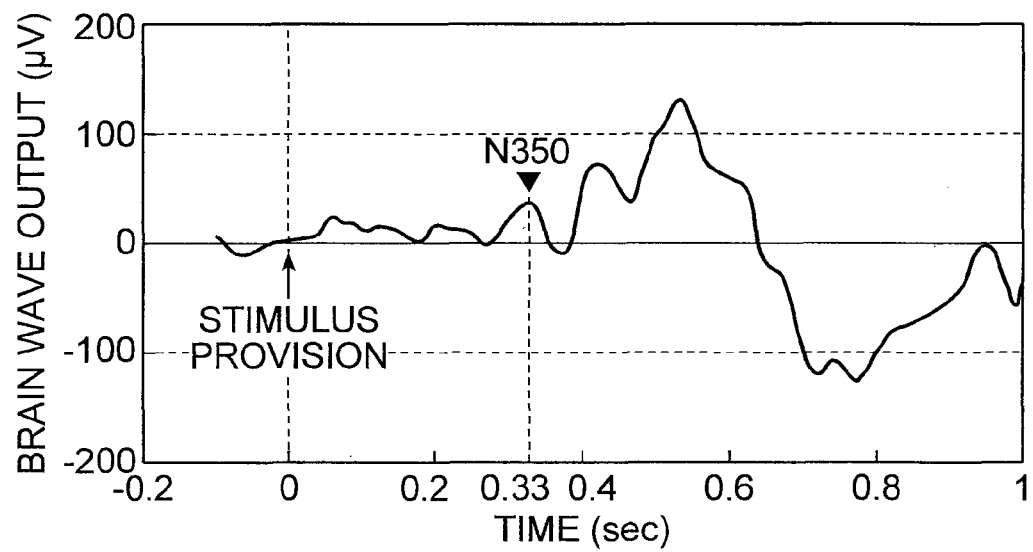

Next, the brain wave indexes of stimulatory effects which surface in the brain waves both when the back seat passenger is awake and when the back seat passenger is asleep while the same stimulus is applied will be described with reference to FIG. 6. FIG. 6 is a diagram showing brain wave indexes for an acoustic stimulus. Specifically, FIG. 6(a) shows brain waves which are measured when the back seat passenger is awake, and FIG. 6(b) shows brain waves which are measured when the back seat passenger is asleep. The brain waves shown in FIG. 6(a) can be measured when an acoustic stimulus is passed in a dazed state while the back seat passenger is awake. The brain waves shown in FIG. 6(b) can be measured through perception of an acoustic stimulus when the back seat passenger is asleep.

With the comparison of FIGS. 6(a) and 6(b), it can be seen that, when the same acoustic stimulus is applied, the brain wave indexes of N350 surface both when the back seat passenger is awake and when the back seat passenger is asleep. For this reason, N350 is specified as the brain wave indexes which surface when the back seat passenger is awake and when the back seat passenger is asleep while the same stimulus is applied, and the latent time, amplitude, or the like of the brain wave indexes are measured, thereby deriving the relationship between the stimulatory effects when the back seat passenger is awake and the stimulatory effects when the back seat passenger is asleep while the same stimulus is applied.

Accordingly, the ECU 5 constructs, as a database, the relationship between the stimulatory effects when the back seat passenger is awake and the stimulatory effects when the back seat passenger is asleep from the brain wave indexes of N350 which surface when the back seat passenger is awake and when the back seat passenger is asleep while the same stimulus is applied, and stores the database in the memory 4.

The ECU 5 creates a conversion model for converting the stimulatory effects when the back seat passenger is awake and the stimulatory effects when the back seat passenger is asleep with reference to the constructed database. The conversion model can be identified from the constructed database using neural net, GA-Fuzzy, Mahalanobis Taguchi System, a threshold value process, or the like.

Next, the specification of stimulatory parameters will be described in detail.

Figure 7:
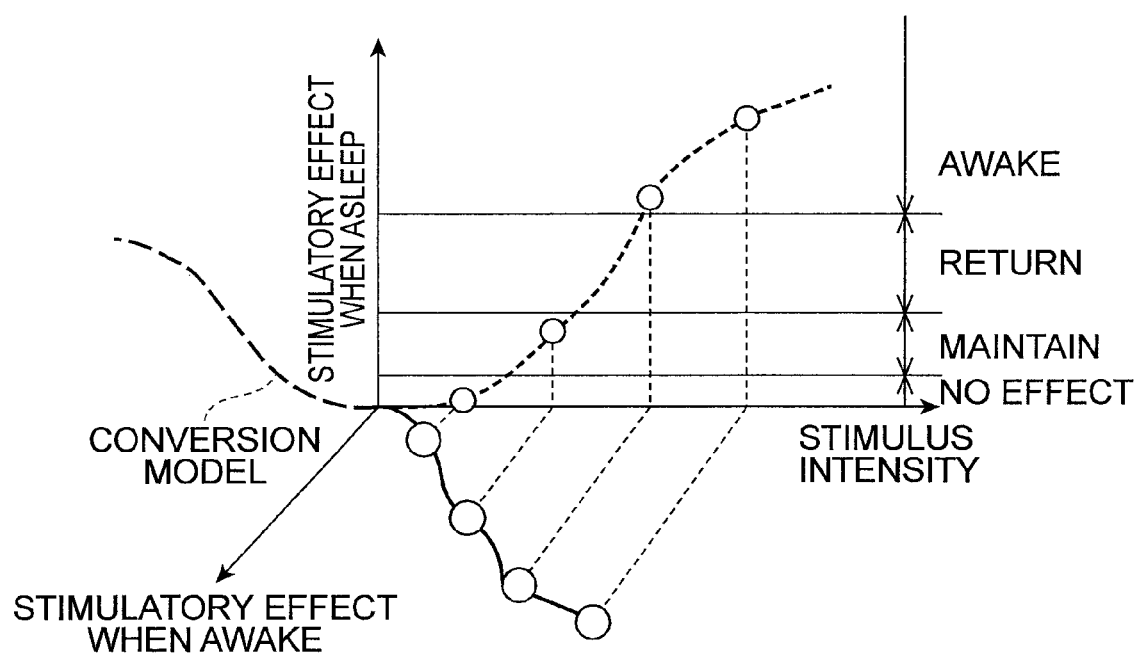
FIG. 7 is a diagram showing a method of selecting parameters of a stimulus.

FIG. 7 is a diagram showing a method of selecting parameters of a stimulus. As shown in FIG. 7, the ECU 5 first measures stimulatory effects for stimuli of various parameters when the back seat passenger is awake. The parameters of a stimulus specify the type of the stimulus, the intensity of the stimulus, or the like. In the case of an acoustic stimulus, the parameters relating to the type of the stimulus include sound, single sound, mechanical sound, music, and the like, and the parameters relating to the intensity of the stimulus include sound volume, sound pressure, frequency, and the like.

Next, the ECU 5 converts the measured stimulatory effects when the back seat passenger is awake to the stimulatory effects when the back seat passenger is asleep using the conversion model, thereby estimating stimulatory effects when a stimulus of each parameter is applied while the back seat passenger is asleep.

Next, the ECU 5 selects the parameters of a stimulus for which a desired stimulatory effect surfaces from the relationship between the stimulatory effects and the changes in the sleep state when the back seat passenger is asleep such that the sleep state of the back seat passenger who takes a short sleep is maintained in a light sleep state. The changes in the sleep state for the stimulatory effects include four types of "no effect", "maintain", "return", and "wake". The type "no effect" means that there is no stimulatory effect even when a stimulus is applied. The type "maintain" means that there is no change in sleep depth even when a stimulus is applied. The type "return" means that, if a stimulus is applied, the sleep depth changes in the wake direction. The type "wake" means that, if a stimulus is applied, the passenger is awake. For this reason, for example, when the sleep depth is II, the parameters of a stimulus for which a stimulatory effect surfaces such that the change in sleep state is "maintain" are selected. When the sleep depth reaches III, the parameters of a stimulus for which a stimulatory effect surfaces such that the change in the sleep state becomes "return" are selected. The relationship between the stimulatory effects and the changes in the sleep state when the back seat passenger is asleep is compiled as a database.

The ECU 5 causes the stimulus generator 3 to generate a stimulus of the selected parameters and maintains the sleep state of the back seat passenger in the light sleep state such that the back seat passenger who takes a short sleep does not fall into a deep sleep.

Next, a process operation of the vehicle control device 1 of this embodiment will be described.

Figure 8:
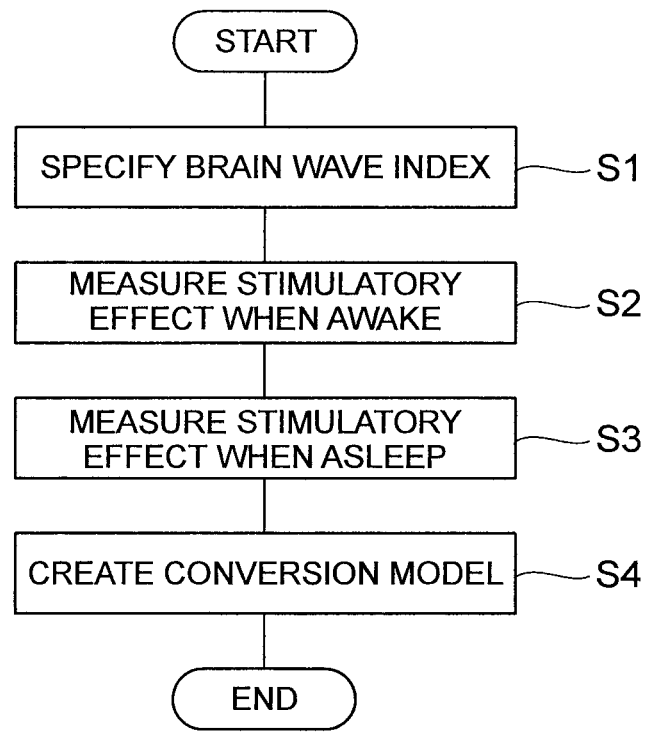
FIG. 8 is a flowchart showing a conversion model creation process.

First, a conversion model creation process will be described with reference to FIG. 8. FIG. 8 is a flowchart showing a conversion model creation process.

As shown in FIG. 8, first, the ECU 5 causes the stimulus generator 3 to generate an acoustic stimulus and acquires the brain wave output of the back seat passenger from the electroencephalogram 2 to specify the brain wave indexes of stimulatory effects which surface in the brain waves when the back seat passenger is awake and when the back seat passenger is asleep while the same stimulus is applied (Step S1). In Step S1, the brain wave indexes of N350 are specified as the brain wave indexes of stimulatory effects which surface in the brain waves when the back seat passenger is awake and when the back seat passenger is asleep while the same stimulus is applied.

Next, the ECU 5 causes the stimulus generator 3 to generate an acoustic stimulus when the back seat passenger is awake and acquires the measured brain wave output of the back seat passenger measured from the electroencephalogram 2. The brain wave indexes are extracted from the acquired brain wave output, and the latent time and amplitude of the extracted brain wave indexes are verified to measure the stimulatory effects when the back seat passenger is awake (Step S2).

Next, the ECU 5 causes the stimulus generator 3 to generate the same acoustic stimulus as in Step S2 when the back seat passenger is asleep, and acquires the measured brain wave output of the back seat passenger from the electroencephalogram 2. The brain wave indexes are extracted from the acquired brain wave output, and the latent time and amplitude of the extracted brain wave indexes are verified to measure the stimulatory effects when the back seat passenger is asleep (Step S3).

The ECU 5 constructs a database which includes the stimulatory effects when the back seat passenger is awake measured in Step S2 and the stimulatory effects when the back seat passenger is asleep measured in Step S3, and stores the database in the memory 4.

The ECU 5 creates a conversion model for converting the stimulatory effects when the back seat passenger is awake and the stimulatory effects when the back seat passenger is asleep with reference to the constructed database, and ends the conversion model creation process (Step S4). As described above, the creation of the conversion model is identified from the constructed database using neural net, GA-Fuzzy, Mahalanobis Taguchi System, a threshold value process, or the like.

Figure 9:
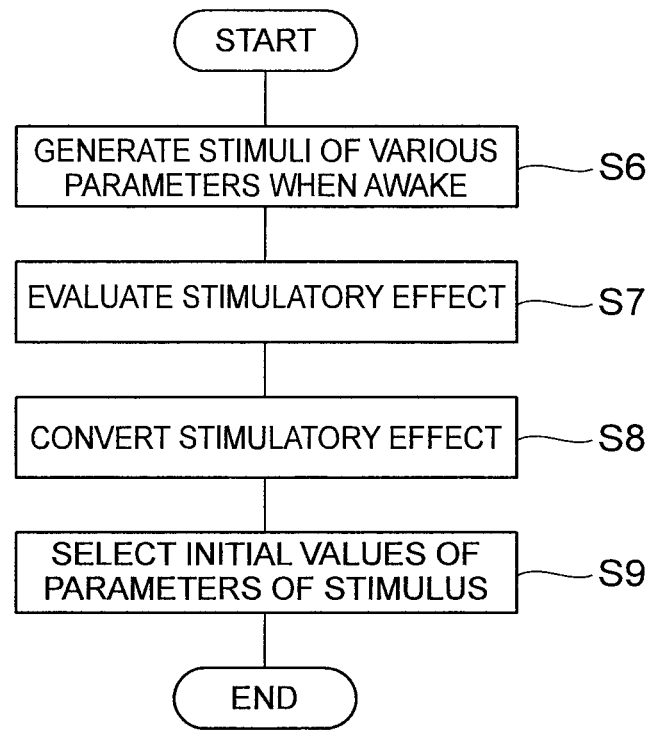
FIG. 9 is a flowchart showing a stimulatory parameter selection process.

Next, a stimulatory parameter selection process will be described with reference to FIG. 9. FIG. 9 is a flowchart showing a stimulatory parameter selection process.

As shown in FIG. 9, first, the ECU 5 causes the stimulus generator 3 to generate a stimulus of various parameters when the back seat passenger is awake (Step S6). As described above, the parameters of a stimulus includes the parameters relating to the type of the stimulus, such as sound, single sound, mechanical sound, and music, and the parameters relating to the intensity of the stimulus, such as sound volume, sound pressure, and frequency. Accordingly, the ECU 5 causes the stimulus generator 3 to generate an acoustic stimulus, such as sound, single sound, mechanical sound, or music, while changing the stimulus intensity, such as sound volume, sound pressure, or frequency.

Next, the ECU 5 acquires the measured brain wave output of the back seat passenger from the electroencephalogram 2, and verifies the latent time and amplitude of the brain wave index surfaced in the brain waves to evaluate stimulatory effects for the stimuli generated in Step S6 (Step S7).

Figure 10:
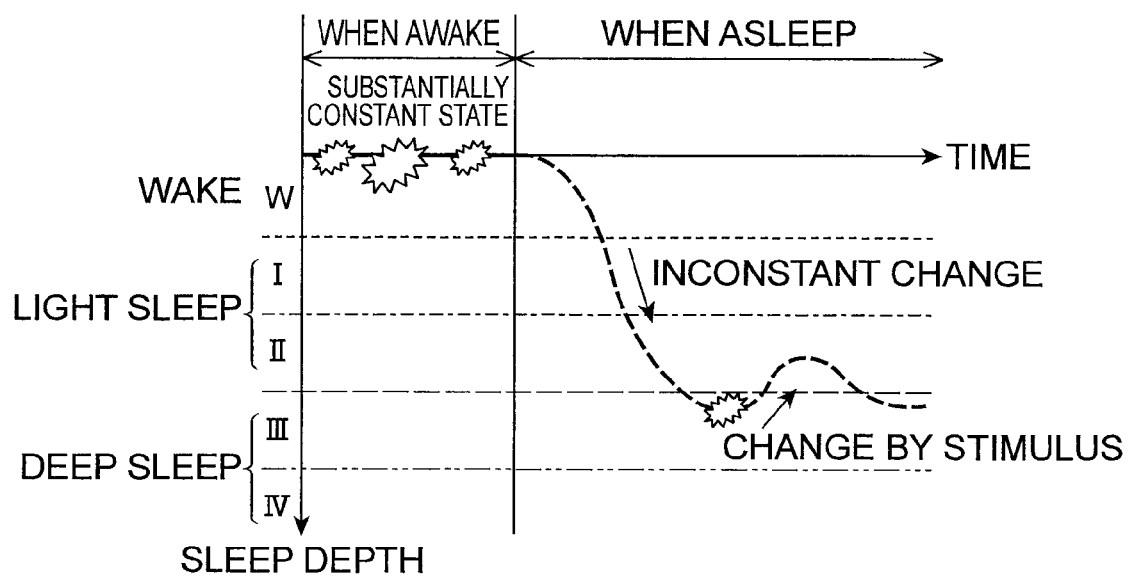
FIG. 10 is a diagram showing the relationship between a stimulus and a change in a sleep state.

Here, the meaning of evaluating stimulatory effects when the back seat passenger is awake will be described with reference to FIG. 10. FIG. 10 is a diagram showing the relationship between a stimulus and a change in the sleep state. As shown in FIG. 10, when the back seat passenger is asleep, if a stimulus is applied, the sleep depth changes. The sleep depth changes inconstantly over time. In this way, when the back seat passenger is asleep, each time a stimulus is generated, the sleep state changes, making it difficult to appropriately evaluate stimulatory effects. Meanwhile, when the back seat passenger is awake, the sleep state is substantially constant, making it possible to appropriately evaluate stimulatory effects. Accordingly, in Steps S6 and S7, when the back seat passenger is awake, stimulatory effects for stimuli of various parameters are evaluated, making it possible to evaluating the effects of the stimuli without being affected by changes in sleep depth.

In Step S7, since the brain wave output from the same person changes depending on the measurement position of the electroencephalogram 2, the physical shape of the back seat passenger, or the like, the stimulatory effects are corrected on the basis of the amplitude of a specific brain wave, and the stimulatory effects when the back seat passenger is awake are evaluated.

Figure 11:
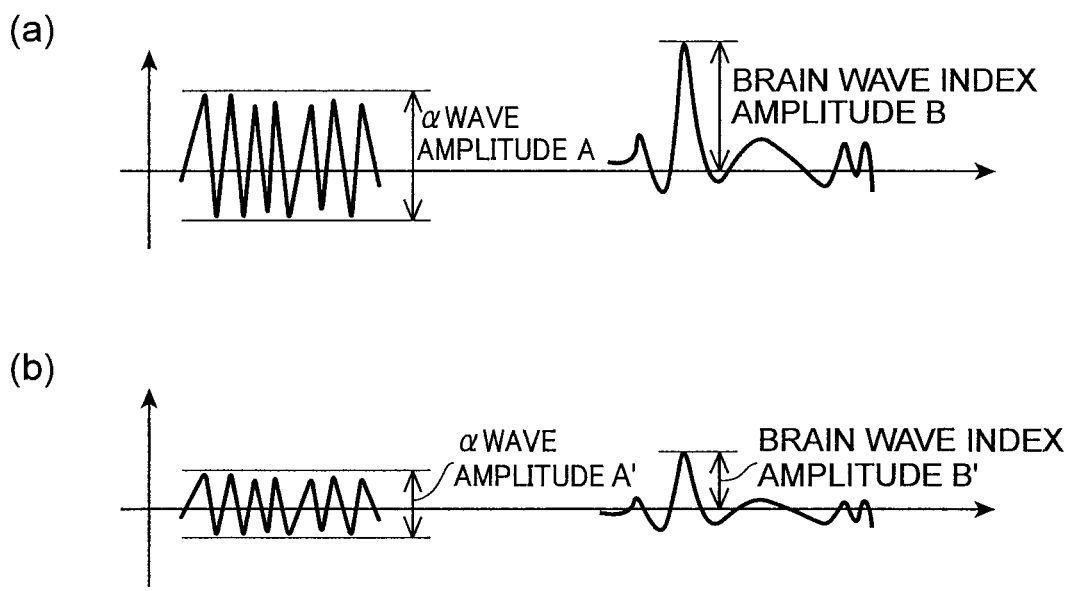
FIG. 11 is a diagram illustrating correction of stimulatory effects.

FIG. 11 is a diagram illustrating correction of stimulatory effects. As shown in FIG. 11, usually, a specific brain wave, such as α wave generated in the eye closure state or the like when the back seat passenger is awake, does not significantly change in amplitude. Accordingly, the stimulatory effects are corrected on the basis of the amount of relative change in the amplitude of the brain wave index with respect to the amplitude of the α waves, and the stimulatory effects when the back seat passenger is awake are evaluated on the basis of the corrected stimulatory effects. Specifically, as shown in FIG. 11(a), if the amplitude of the α wave and the amplitude of the brain wave index at a certain point of time are respectively A and B, and as shown in FIG. 11(b), if the amplitude of the α wave and the amplitude of the brain wave index are respectively A' and B', the stimulatory effects when the back seat passenger is awake are evaluated by B/A and B'/A'. Therefore, it is possible to absorb an intraindividual difference due to a brain wave measurement method, a physical shape, or the like.

In Step S7, even if the intraindividual difference due to the brain wave measurement method, the physical shape, or the like is absorbed, the brain wave output changes from person to person. Thus, the amplitude of the brain wave is standardized using the non-individual-based absolute reference, and the stimulatory effects when the back seat passenger is awake are evaluated.

Figure 12:
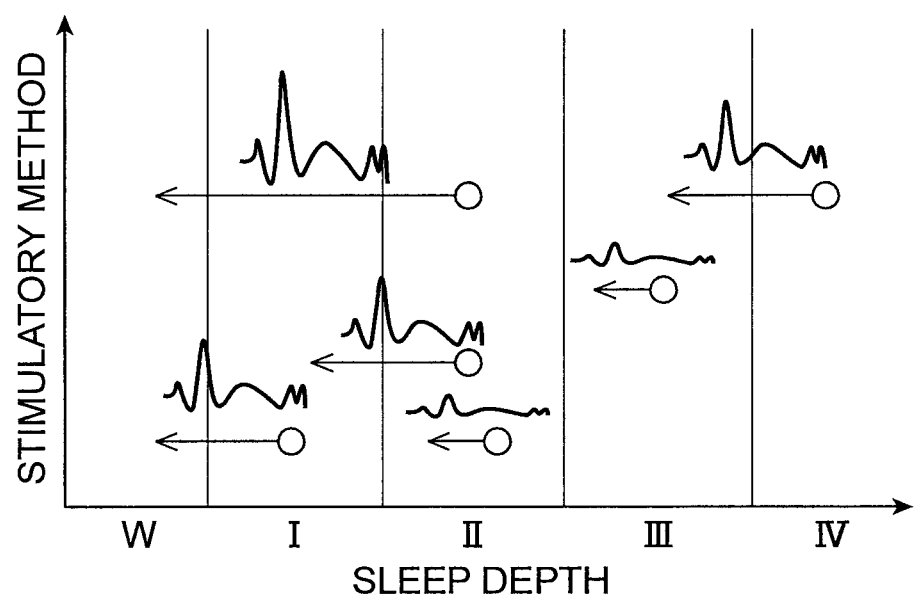
FIG. 12 is a diagram showing the relationship between the amplitude of a brain wave index and the amount of change in sleep depth.

FIG. 12 is a diagram showing the relationship the amplitude of a brain wave index and the amount of change in sleep depth. As shown in FIG. 12, the sleep depth is used as a non-individual-based evaluation method based on the international standard. Accordingly, the amplitude of the brain wave index is corrected on the basis of the amount of change in sleep depth. Thus, it is possible to absorb the intraindividual difference.

Next, the ECU 5 converts the stimulatory effects when the back seat passenger is awake evaluated in Step S7 to the stimulatory effects when the back seat passenger is asleep using the conversion model, and estimates stimulatory effects when a stimulus of each parameter is applied while the back seat passenger is asleep (Step S8).

The ECU 5 selects the parameters of a stimulus for which desired stimulatory effects surface from the relationship between the stimulatory effects and the changes in the sleep state when the back seat passenger is asleep such that the sleep state of the back seat passenger who takes a short sleep is maintained in the light sleep state, and ends the stimulatory parameter selection process (Step S9). The parameters of a stimulus selected in Step S9 become the initial values of a stimulus which is generated by the stimulus generator 3.

Figure 13:
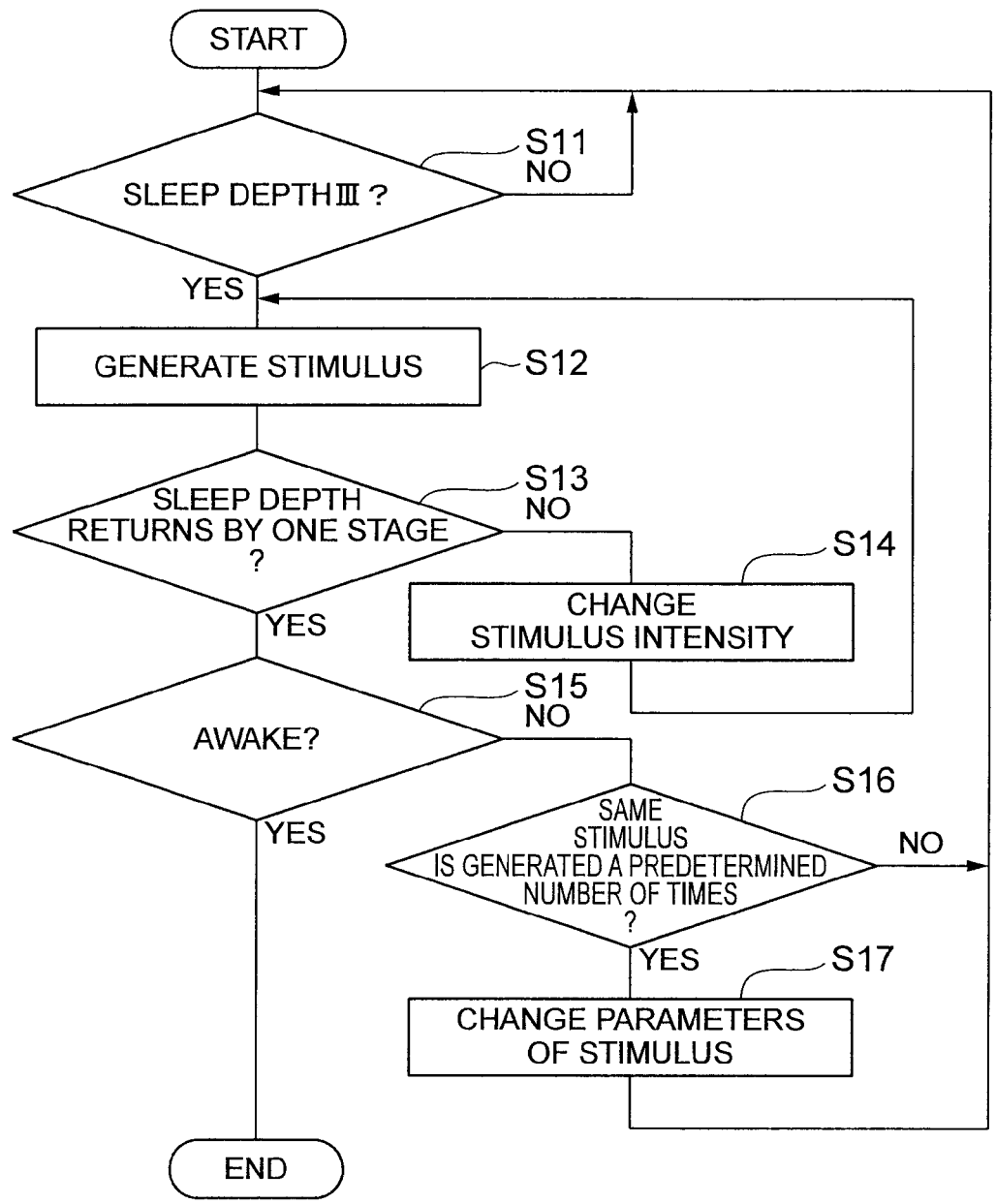
FIG. 13 is a flowchart showing a stimulus generation process.

Next, a stimulus generation process will be described with reference to FIG. 13. FIG. 13 is a flowchart showing a stimulus generation process.

As shown in FIG. 13, the vehicle control device 1 first estimates the sleep depth of the back seat passenger who takes a short sleep, and determines whether or not the sleep depth reaches III (Step S11).

Figure 14:
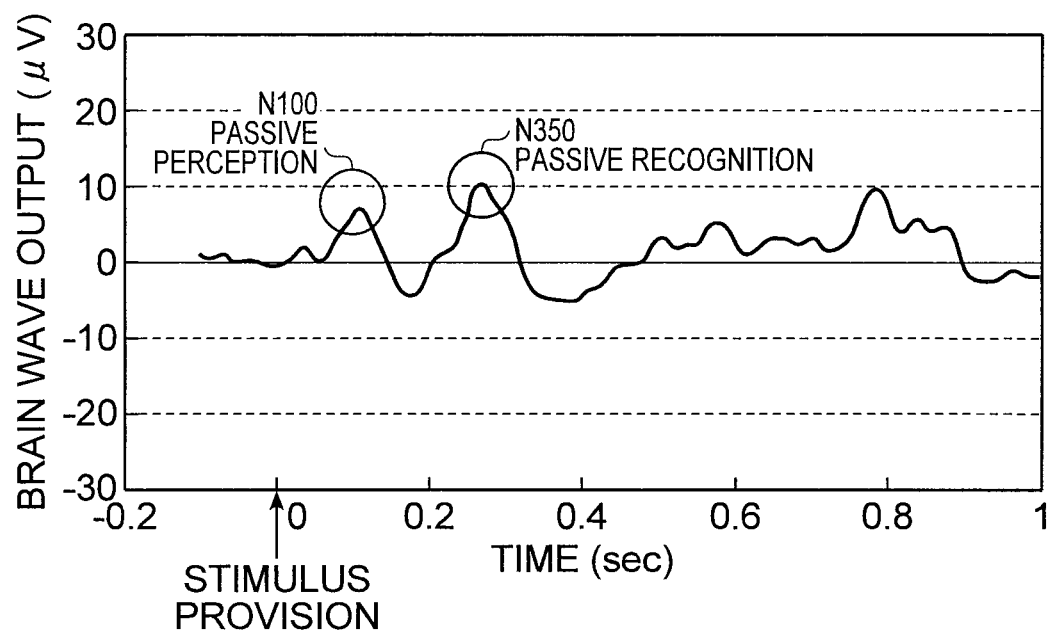
FIG. 14 is a diagram showing a brain wave index for a stimulus.
Figure 15:
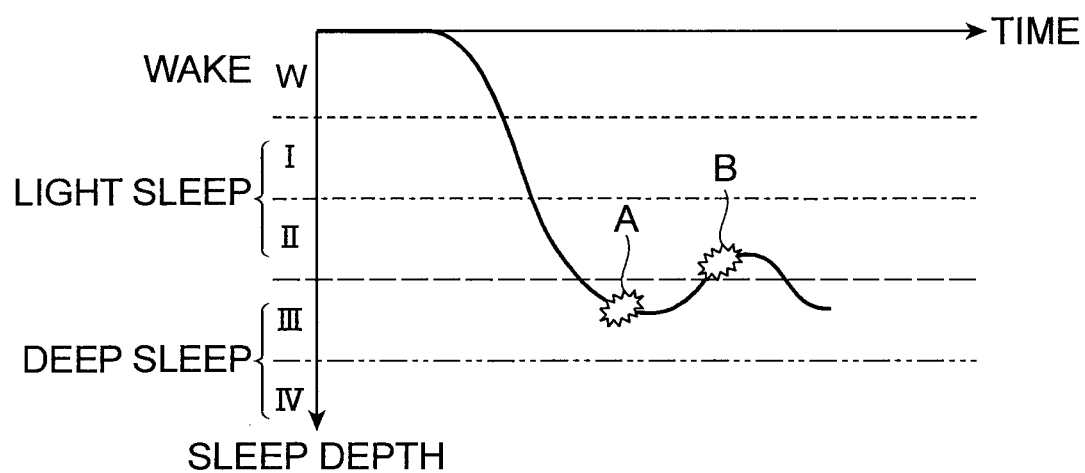
FIG. 15 is a diagram showing the relationship between stimulus generation timing and sleep depth.

Here, a sleep depth estimation method will be described with reference to FIGS. 14 to 16. FIG. 14 is a diagram showing a brain wave index for a stimulus. FIG. 15 is a diagram showing the relationship between stimulus generation timing and sleep depth. FIG. 16 is a diagram showing the relationship between the presence/absence of appearance of a brain wave index and sleep depth.

As shown in FIG. 14, if a stimulus is generated by the stimulus generator 3 and applied to the back seat passenger, and the brain wave indexes of N100 which reflect passive perception and the brain wave indexes of N350 which reflect passive recognition are induced from the brain wave output measured by the electroencephalogram 2. Like a stimulus B of FIG. 15, if a stimulus is applied in the light sleep state, the brain wave indexes of N100 and the brain wave indexes of N350 are induced. Meanwhile, like a stimulus A of FIG. 15, if a stimulus is applied in the deep sleep state, only the brain wave indexes of N350 are induced, and the brain wave indexes of N100 are not induced.

Accordingly, as shown in FIG. 16, the ECU 5 causes the stimulus generator 3 to generate a stimulus when the back seat passenger is asleep, and when the brain wave indexes of N100 and the brain wave indexes of N350 are observed from the brain waves measured by the electroencephalogram 2, determines that the passenger takes a light sleep. When the brain wave indexes of N350 are observed and the brain wave indexes of N100 are not observed from the brain waves measured by the electroencephalogram 2, the ECU 5 determines that the passenger takes a light sleep.

If it is determined that the sleep depth reaches III (Step S11: YES), the ECU 5 causes the stimulus generator 3 to generate a stimulus of the parameters selected in Step S9 (Step S12).

Next, the ECU 5 estimates the sleep depth of the back seat passenger, and determines whether or not the sleep depth returns by one stage in the wake direction (Step S13). With regard to the estimation of the sleep depth in Step S13, similarly to the estimation of the sleep depth in Step S12, determination is made on the basis of the presence/absence of appearance of the brain wave indexes of N100 and N350 which surface when a stimulus is applied to the back seat passenger.

If it is determined that there is no change in sleep depth (Step S13: NO), the ECU 5 changes the parameters of the stimulus such that the stimulus intensity increases (Step S14), returns to Step S12, and generates a stimulus of the changed parameters.

If it is determined that the sleep depth returns by one stage (Step S13: YES), the ECU 5 determines whether or not the back seat passenger is awake (Step S15).

If it is determined that the back seat passenger is awake (Step S15: YES), the ECU 5 ends the stimulus generation process.

If it is determined that the back seat passenger is not awake (Step S15: NO), the ECU 5 determines whether or not a stimulus of the same parameters is generated a predetermined number of times (Step S16).

If it is determined that a stimulus of the same parameters is generated smaller than a predetermined number of times (Step S16: NO), the ECU 5 returns to Step S11 and repeats the above-described process.

If it is determined that a stimulus of the same parameters is generated a predetermined number of times (Step S16: YES), the ECU 5 changes the parameters of the stimulus (Step S17).

Figure 17:
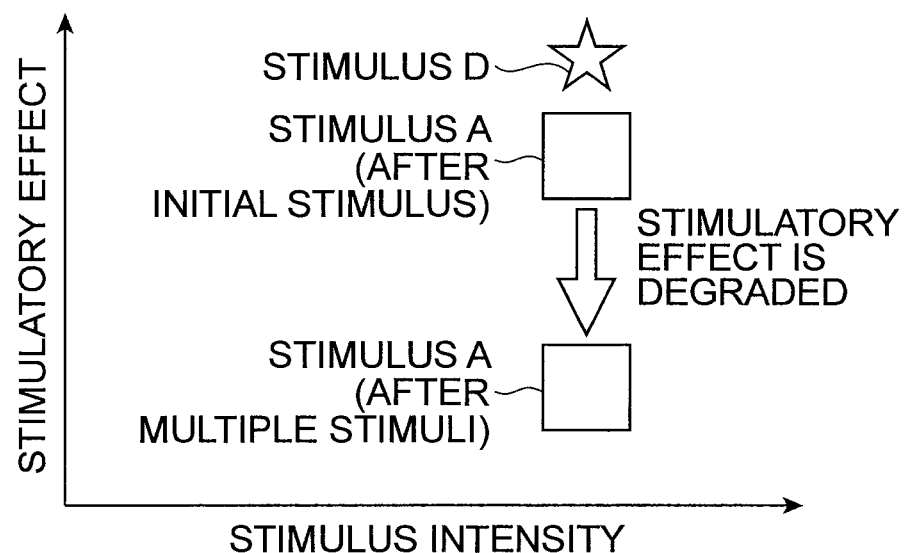
FIG. 17 is a diagram showing the state of adaptation for the same stimulus.

Here, the meaning of changing the parameters of a stimulus will be described with reference to FIG. 17. FIG. 17 is a diagram showing the state of adaptation for the same stimulus. As shown in FIG. 17, if a stimulus (a stimulus A of FIG. 17) of predetermined parameters is generated, high stimulatory effects surface initially, as the number of generations increases, the back seat passenger is being adapted to the stimulus, and the stimulatory effects are degraded. Accordingly, if a stimulus of the same parameters is generated a predetermined number of times, a stimulus (a stimulus D of FIG. 17) of different parameters is generated, thereby suppressing degradation in the stimulatory effects to apply appropriate stimulatory effects. The parameters of a stimulus are changed such that stimulatory effects for a stimulus of parameters after change are comparable with stimulatory effects for a stimulus of parameters before change.

If the parameters of a stimulus are changed in Step S17, the ECU 5 returns to Step S11 and generates a stimulus of the changed parameters.

As described above, according to the vehicle control device 1 of the first embodiment, the brain wave indexes of stimulatory effects which surface in response to the stimuli both when the back seat passenger is awake and when the back seat passenger is asleep are specified, thereby associating the stimulatory effects when the back seat passenger is awake with the stimulatory effects when the back seat passenger is asleep. Therefore, it is possible to convert the stimulatory effects between when the back seat passenger is awake and when the back seat passenger is asleep, thereby converting the stimulatory effects when the back seat passenger is asleep from the stimulatory effects when the back seat passenger is awake.

The brain wave indexes which surface when the back seat passenger is awake and when the back seat passenger is asleep while the same stimulus is applied are specified, thereby creating the conversion model for converting the stimulatory effects when the back seat passenger is awake and the stimulatory effects when the back seat passenger is asleep. With the use of the created conversion model, it is possible to estimate the stimulatory effects when the back seat passenger is asleep from the stimulatory effects when the back seat passenger is awake. Accordingly, a stimulus which is applied to the back seat passenger is obtained on the basis of the relationship between the stimulatory effects and the changes in sleep depth, thereby controlling the sleep depth of the back seat passenger and maintaining the sleep state of the back seat passenger in the light sleep state.

The stimulatory effects are corrected on the basis of the amount of relative change in the amplitude of the brain wave indexes with respect to the amplitude of a specific brain wave, thereby excluding the influence of a measurement error of a brain wave measurement unit, the physical shape of the back seat passenger, or the like and appropriately estimating the stimulatory effects when the back seat passenger is asleep.

The parameters of a stimulus which is applied when the back seat passenger is asleep are selected on the basis of the stimulatory effects when the back seat passenger is awake, thereby excluding the influence of a change in the sleep state of the back seat passenger when selecting a stimulus which is applied to the back seat passenger.

If a stimulus of the same parameters is generated a predetermined number of times, the parameters of the stimulus are changed, thereby preventing the stimulatory effects from being degraded habitually.

The sleep depth is estimated on the basis of the response of the brain waves for a stimulus applied to the back seat passenger, thereby improving the estimation precision of the sleep depth without being affected by the estimation timing of the sleep depth.

[Second Embodiment]

Next, a second embodiment will be described. A vehicle control device of the second embodiment selects the parameters of a stimulus which is applied when the back seat passenger is asleep on the basis of stimulatory effects for a stimulus of different parameters in the stimulatory parameter selection process. In particular, the parameters of a stimulus for which high stimulatory effects surface from among the stimuli with the same stimulus intensity are selected. For this reason, only the stimulatory parameter selection process will be hereinafter described.

Figure 18:
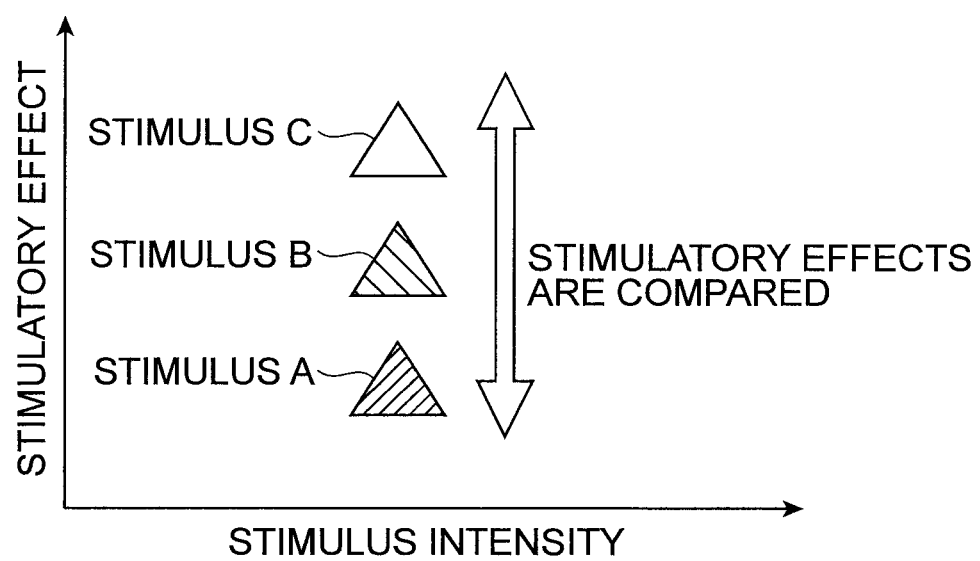
FIG. 18 is a diagram showing different types of stimuli with the same intensity.

As shown in FIG. 9, in the stimulatory parameter selection process, first, the ECU 5 causes the stimulus generator 3 to generate stimuli of various parameters when the back seat passenger is awake (Step S6). At this time, as shown in FIG. 18, different types of stimuli with the same stimulus intensity are generated.

Next, the ECU 5 acquires the measures brain wave output of the back seat passenger from the electroencephalogram 2 and verifies the latent time and amplitude of the brain wave indexes surfaced in the brain waves to evaluate stimulatory effects for the stimuli generated in Step S6 (Step S7).

At this time, the parameters of a stimulus for which the highest stimulatory effect surface from among the stimuli with the same stimulus intensity are extracted.

Figure 19:
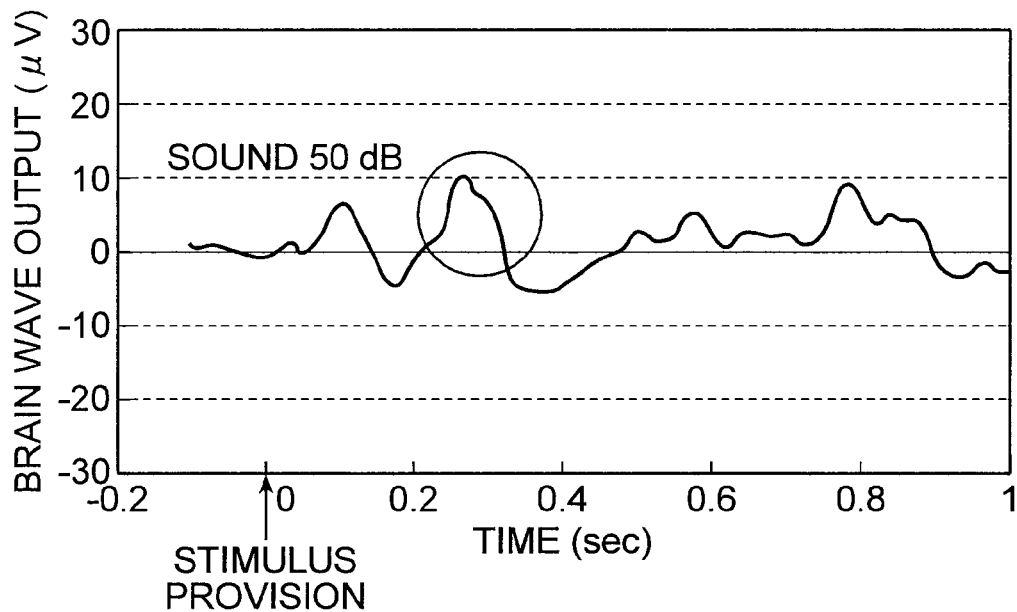
FIG. 19 is a diagram showing a brain wave index for an acoustic stimulus, specifically, FIG. 19(*a*) shows a brain wave index for a stimulus of sound of 50 dB, and FIG. 19(*b*) shows a brain wave index for a stimulus of single sound of 50 dB.
Figure 19:
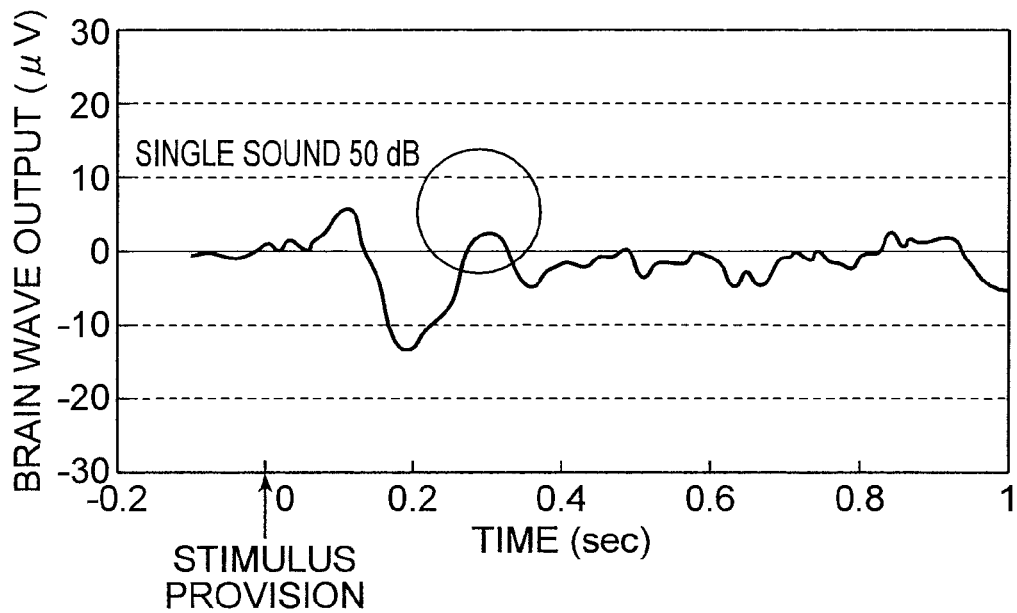

FIG. 19 is a diagram showing a brain wave index for an acoustic stimulus. Specifically, FIG. 19(*a*) shows a brain wave index for a stimulus of sound of 50 dB, and FIG. 19(*b*) shows a brain wave index for a stimulus of single sound of 50 dB. FIG. 19 is a diagram showing different types of stimuli with the same intensity.

As shown in FIGS. 19(*a*) and 19(*b*), with the observation of the brain wave indexes when stimuli with the same intensity of 50 dB are applied, it can be seen that stimulatory effects for a stimulus of sound are higher than stimulatory effects for a stimulus of single sound.

Accordingly, in Step S7, the ECU 5 compares the stimulatory effects for a plurality of stimuli with the same stimulus intensity, and extracts the parameters of a stimulus for which the highest stimulatory effects surface.

Next, the ECU 5 converts the stimulatory effects when the back seat passenger is awake evaluated in Step S7 to the stimulatory effects when the back seat passenger is asleep using the conversion model, and estimates stimulatory effects when a stimulus of each parameter is applied while the back seat passenger is asleep (Step S8). In Step S8, the parameters of the stimulus extracted in Step S7 are used.

The ECU 5 selects the parameters of a stimulus for which desired stimulatory effects surface from the relationship between the stimulatory effects and the changes in the sleep state when the back seat passenger is asleep such that the sleep state of the back seat passenger who takes a short sleep is maintained in the light sleep state, and ends the stimulatory parameter selection process (Step S9).

As described above, according to the vehicle control device of the second embodiment, when there are a plurality of stimuli with the same intensity, the parameters of a stimulus for which the highest stimulatory effects surface from among the stimuli are utilized, thereby efficiently generating a stimulus.

[Third Embodiment]

Next, a third embodiment will be described. A vehicle control device of the third embodiment selects the parameters of a stimulus which is applied when the back seat passenger is asleep on the basis of stimulatory effects for a stimulus of different parameters in the stimulatory parameter selection process. In particular, the parameters of a stimulus with low stimulus intensity from among the stimuli having the same stimulatory effects are selected. For this reason, only the stimulatory parameter selection process will be hereinafter described.

Figure 20:
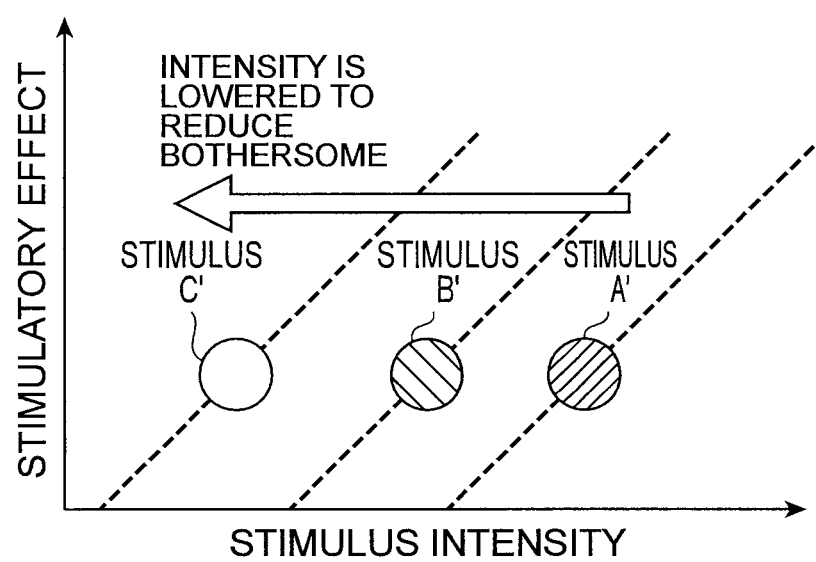
FIG. 20 is a diagram showing stimuli of different intensities with the same stimulatory effect.

As shown in FIG. 9, in the stimulatory parameter selection process, first, the ECU 5 causes the stimulus generator 3 to generate stimuli of various parameters when the back seat passenger is awake (Step S6). At this time, as shown in FIG. 20, stimuli for which the same stimulatory effects are obtained with different stimulus intensities are generated.

Next, the ECU 5 acquires the measured brain wave output of the back seat passenger from the electroencephalogram 2, and verifies the latent time and amplitude of the brain wave indexes surfaced in the brain waves to evaluate stimulatory effects for the stimuli generated in Step S6 (Step S7).

At this time, the parameters of a stimulus with the lowest stimulus intensity from among the stimuli having the same stimulatory effects are extracted. That is, in Step S7, the ECU 5 compares the stimulus intensities of a plurality of stimuli having the same stimulatory effects, and extracts the parameters of a stimulus with the lowest stimulus intensity.

Next, the ECU 5 converts the stimulatory effects when the back seat passenger is awake evaluated in Step S7 to the stimulatory effects when the back seat passenger is asleep using the conversion model, and estimates stimulatory effects when a stimulus of each parameter is applied while the back seat passenger is asleep (Step S8). In Step S8, the parameters of the stimulus extracted in Step S7 are used.

The ECU 5 selects the parameters of a stimulus for which desired stimulatory effects surface from the relationship between the stimulatory effects and the changes in the sleep state when the back seat passenger is asleep such that the sleep state of the back seat passenger who takes a short sleep is maintained in the light sleep state, and ends the stimulatory parameter selection process (Step S9).

As described above, according to the vehicle control device of the third embodiment, when there are a plurality of stimuli having the same stimulatory effects, a stimulus with the lowest stimulus intensity is selected, thereby reducing bothersome imposed on a driver or the like who does not take a short sleep and selecting a stimulus with a little sense of discomfort without degrading the stimulatory effects.

Although the preferred embodiments of the invention have been described, the invention is not limited to the foregoing embodiments. For example, although in the foregoing embodiments, a case where the sleep state of the back seat passenger is controlled has been described, a person to be controlled may be any person who gets into a vehicle, or may be a driver who takes a short sleep, a front seat passenger, or the like.

Although in the foregoing embodiments, a case where the stimulatory effect estimation device according to the invention is mounted in the vehicle control device has been described, for example, in various fields, such as a sleep in a sleeping room or medicine in a medical facility, stimulatory effects when the back seat passenger is asleep may be estimated using a conversion model, and a subject may be maintained in the light sleep state.

Although in the foregoing embodiments, a case where the conversion model is created in the vehicle control device 1 has been described, the brain wave indexes which surface when the back seat passenger is awake and when the back seat passenger is asleep while the same stimulus is applied may be measured to create a conversion model in advance, and the vehicle control device 1 may estimate the stimulatory effects when the back seat passenger is asleep from the stimulatory effects when the back seat passenger is awake using the created conversion model.

Although in the foregoing embodiments, a case where the sleep state is determined on the basis of whether or not the brain wave indexes for a stimulus are observed, as in the related art, the determination may be made on the basis of the content of δ waves in the brain waves.

Industrial Applicability

According to the stimulatory effect estimation device, the stimulatory effect estimation method, and the vehicle control device of the invention, it is possible to estimate the stimulatory effects when the back seat passenger is asleep. According to the sleep depth estimation device and the vehicle control device of the invention, it is possible to estimate the sleep depth with high precision without being affected by the estimation timing of the sleep depth. According to the vehicle control device of the invention, it is possible to control the sleep depth of the passenger.

Reference Signs List

1: vehicle control device (stimulatory effect estimation device, sleep depth estimation device)
2: electroencephalogram
3: stimulus generator
4: memory
5: ECU (stimulatory effect estimation unit, sleep depth estimation unit)

The invention claimed is:

1. A stimulatory effect estimation device comprising:
a stimulus generation unit which applies a stimulus to a subject;
a brain wave measurement unit which measures the brain waves of the subject; and
a stimulatory effect estimation unit which specifies brain wave indexes of stimulatory effects which surface in response to the stimuli both when the subject is awake and when the subject is asleep from the brain waves measured by the brainy wave measurement unit when a stimulus is plied from the stimulus generation unit while the subject is awake and the brain waves, measured by the brain wave measurement unit when a stimulus is applied from the stimulus generation unit while the subject is asleep;
wherein the stimulatory effect estimation unit estimates stimulatory effects when the subject is asleep from stimulatory effects when the subject is awake using a conversion model that converts the stimulatory effect when the subject is awake to the stimulatory effects when the subject is asleep on the basis of the brain wave indexes which surface when the same stimulus is applied when the subject is awake and when the subject is asleep, and selects a stimulus which is applied to the subject on the basis of a relationship between the stimulatory effects and changes in sleep depth when the subject is asleep.

2. The stimulatory effect estimation device according to claim 1,
wherein the stimulatory effect estimation unit corrects the stimulatory effects on the basis of the amplitude of a specific brain wave.

3. The stimulatory effect estimation device according to claim 1,
wherein the stimulatory effect estimation unit selects the parameters of a stimulus which is applied when the subject is asleep on the basis of the stimulatory effects when the subject is awake.

4. The stimulatory effect estimation device according to claim 3,
wherein the stimulatory effect estimation unit selects the parameters of a stimulus which is applied when the subject is asleep on the basis of stimulatory effects for a stimulus of different parameters.

5. The stimulatory effect estimation device according to claim 3,
wherein the stimulatory effect estimation unit changes the parameters of a stimulus which is applied when the subject is asleep on the basis of stimulatory effects when a stimulus of a specific parameter continues to be applied.

6. The stimulatory effect estimation device according to claim 1,
wherein the stimulatory effect estimation unit estimates the sleep depth of the subject on the basis of the measurement result of brain waves to a stimulus applied to the subject.

7. A computer-implemented stimulatory effect estimation method comprising the steps of:
generating, using a stimulus generation unit, a stimulus when the subject is awake to acquire the brain waves of the subject;
generating, using the stimulus generation unit, a stimulus when the subject is asleep to acquire the brain waves of the subject; and
specifying, using a stimulatory effect estimation unit, the brain wave indexes of stimulatory, effects which surface in response to the stimuli both when the subject is awake and when the subject is asleep
wherein stimulatory effects when the subject is asleep are estimated from stimulatory effects when the subject is awake using a conversion model that converts the stimulatory effect when the subject is awake to the stimulatory effects when the subject is asleep on the basis of the brain wave indexes which surface when the same stimulus is applied when the subject is awake and when the subject is asleep, and a stimulus which is applied to the subject is selected on the basis of a relationship between the stimulatory effects and changes in sleep depth when the subject is asleep.

* * * * *